United States Patent [19]

Bennett

[11] Plant 4,769

[45] Sep. 29, 1981

[54] MINIATURE ROSE PLANT

[76] Inventor: Cecilia L. D. Bennett, 489 Minot Ave., Chula Vista, Calif. 92010

[21] Appl. No.: 134,941

[22] Filed: Mar. 28, 1980

[51] Int. Cl.[3] ..... A01H 5/00

[52] U.S. Cl. ..... Plt./7

[58] Field of Search ..... Plt./7, 9

*Primary Examiner*—Robert E. Bagwill

[57] ABSTRACT

The subject of the present disclosure is a new and distinct variety of miniature rose plant characterized by the delicate blending of soft pink and soft apricot plus high center and excellent rose form.

1 Drawing Figure

The present invention relates to a new and distinct variety of a bush type rose plant of miniature class; the variety showing a resemblance to Helen Traubel, a hybrid tea variety (U.S. Plant Pat. No. 1,080, expired).

The variety is further characterized by:

Mostly one to a stem blooms held erect on sturdy, straight stems.

Has a pleasant fragrance.

The plant is a vigorous spreading plant. The foliage is a medium green with a fine edge of red; the buds and flowers are similar to Helen Traubel, a delicate pink, apricot color; the blooms hold their shape indefinitely, so retain their beauty.

The plant ranges in size from 12–18 inches, will get slightly larger when planted in the ground.

The plant has good growing habits, has a spreading tendency. A very compact plant with numerous repeat blooms, an attractive plant.

The present variety of miniature rose was originated by me at Tiny Petal's Nursery located at Chula Vista, Calif., under careful observation, and is a cross of Sheri Anne (U.S. Plant Pat. No. 2,836) a miniature as the pollen parent and Little Darling, a floribunda (U.S. Plant Pat. No. 1,581) the seed parent.

Subsequent to origination of the variety I successfully reproduced it at Tiny Petal's Nursery located at aforesaid with reproductions coming true in all respects.

The color photographs illustrate the variety.

Referring now specifically to the new and distinct variety of miniature rose plant, the following is a detailed description thereof in outline; all major color plate identifications being by reference to the British Colour Council Horticultural Colour Chart. Color chart used except where common terms of color definition are employed.

Type: Hardy; compact; seedling; greenhouse; potted plant; garden decoration; cut flowers; exhibition.

Class: Miniature.

Variety name: "Peachy Keen".

Flowers borne: Usually one to a stem on straight, sturdy stems.

Quantity of bloom: Abundant both inside and outside of the greenhouse.

Bud:

*Peduncle.*—Medium to long; sturdy; erect; reddish-green.

*Hairs.*—Minute.

*Before calyx breaks.*—Size — small. Form short; pointed with a few foliaceous apendages and numerous minute hairs on surface of bud; with foliaceous parts extending beyond the tip of the bud equal to one eighth of an inch. Color — medium green opening to a color of near soft apricot, 609/3 page 70. Yellow at the base of the petals. Opening: opens well in all weather.

Bloom:

*Size when fully open.*—Small, averaging about 1½". Petalage — double — averaging about 20 petals, arranged regularly plus sometimes a few petaloids. Form — high centered, opening slowly with a slight roll on the top of the petals. Excellent exhibition form. Flower opens to show stamens.

Petals: Fairly thick; lots of substance; satiny on inside and outside surface.

*Shape.*—Outside petals, broad lanceolate with rounded tip plus (short) acute tip; intermediate — broad lanceolate with rounded tip, plus acute tip; inside petals — broad lanceolate with tip.

Color: Newly opened flower from a flower grown outdoors, Chula Vista, Calif.:

*Outer petals, upper surface.*—Near soft apricot 609/3 page 70, blending to a near French rose 520/3 page 136.

*Outer petal, under surface.*—A near soft apricot 609/3 page 70, with an occasional brushing of near soft scarlet, 19/2 page 19.

*Intermediate petals, upper surface.*—Near soft apricot 609/3 page 70, blending to a near French rose 520/3 page 136.

*Intermediate petals, under surface.*—Near soft apricot 609/3 page 70.

*Inner petals, upper surface.*—A near soft apricot 609/3 page 70, blending to a near French rose 520/3 page 136.

*Inner petals, under surface.*—A near soft apricot 609/3 page 70.

*General color effect.*—Newly opened blooms have a delicate pinkish-apricot glow with a delicate blending of the aforementioned colors.

*Behavior.*—Opens well in all weather. Flowers fade slowly to a Naples yellow 403/3 page 121, blending to a Shell pink 516/1 page 135 on the petal edges. (upper surface) Naples yellow 403/3 page 121, blending to Orient pink 416/3 page 124 on the under surface using the "British Colour Council Horticultural Colour Chart." Stamens reflex, but petals stay erect at all stages and do not reflex downward.

Reproductive organs:

*Stamens.*—Abundant, arranged evenly around pistil.

*Filaments.*—Long, yellow, varying lengths.

*Anthers.*—Well formed: yellow.

*Pollen.*—A lot.

*Pistils.*—A lot.

*Styles.*—Fairly even; greenish.

*Ovaries.*—All encased in calyx.

*Seed.*—A goodly amount.

Foliage:

*Leaves.*—Compound of five (an occasional seven) leaflets; fairly small; leathery; semi-glossy.

*Leaflets.*—Shape: very broad, nearly oval; apex acute; base rounded. Margin serrated.

*Color.*—Medium green with red on outer petals of the newer foliage.

*Rachis.*—Medium length; upper side grooved; under side very few prickles.

*Stipules.*—Medium length; medium width; narrow; short which curve out.

Growth:

*Habit.*—Dwarf; spreading but compact; much branched.

*Growth.*—Free vigorous.

*Canes.*—Long; slender but sturdy; straight.

*Main stems.*—Color: medium green.

*Thorns.*—Average amount; slender; straight; color: reddish.

*Prickles.*—None.

*Hairs.*—None.

Branches:

*Color.*—Medium green.

*Thorns.*—Moderate number; medium length; slender; nearly straight, inclined upward. Medium oval base.

*Prickles.*—None.

*Hairs.*—None.

The miniature rose described herein and its flowers may vary in slight detail due to climatic, soil and cultural conditions under which the variety may be grown; the present description being of the variety as grown at Chula Vista, Calif.

The following is claimed:

1. A new and distinct variety of miniature rose plant of dwarf, hardy, bushy, rounded, much branched habit, substantially as illustrated and described, characterized by buds and flowers of a delicate apricot color near 609/3 and rose 520/3 and flower resembling the variety Helen Traubel a hybrid tea variety, (U.S. Plant Pat. No. 1,080, expired), in form and color, and further characterized by a plant of vigorous and compact growth habit, easy to propagate from cuttings or by budding, with a goodly amount of medium size semi-glossy foliage and an abundance of flowers borne singly on erect stems.

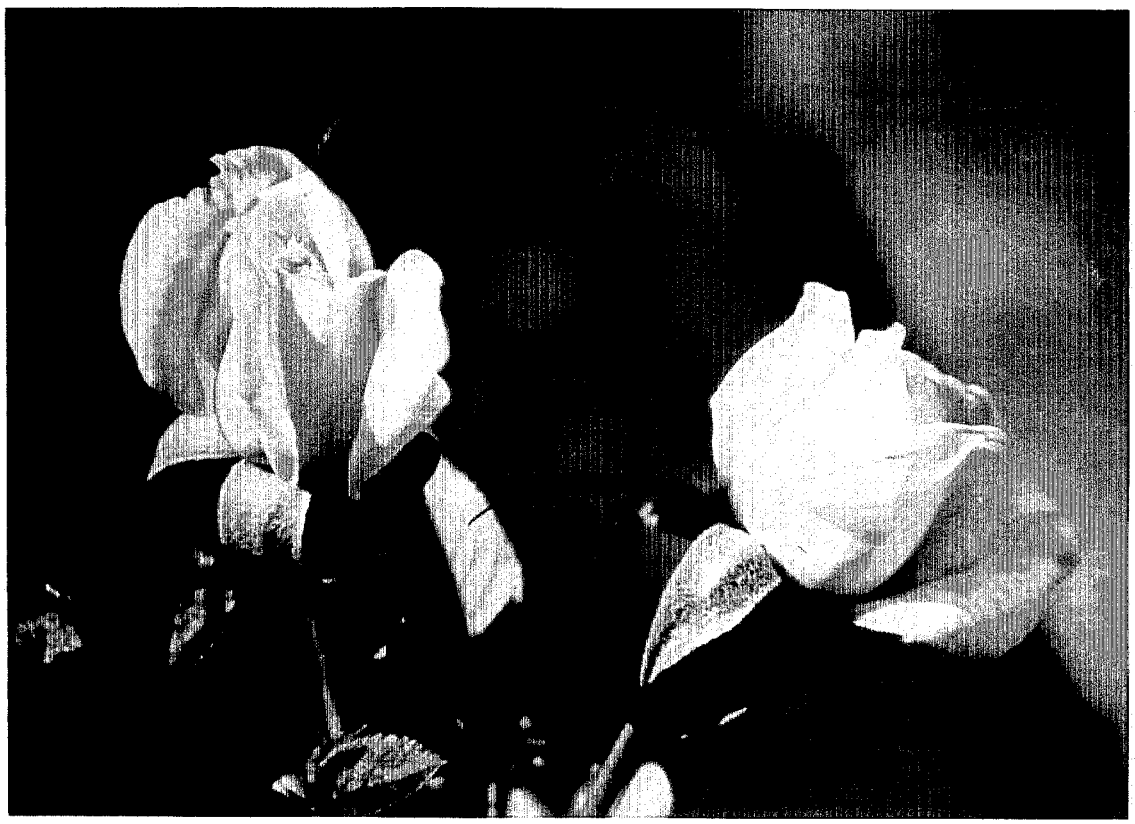

* * * * *